United States Patent [19]

Lutenegger

[11] Patent Number: 4,539,851
[45] Date of Patent: Sep. 10, 1985

[54] SOIL AND ROCK SHEAR TESTER

[75] Inventor: Alan J. Lutenegger, Potsdam, N.Y.

[73] Assignee: Iowa State University Research Foundation, Inc., Ames, Iowa

[21] Appl. No.: 612,708

[22] Filed: May 21, 1984

[51] Int. Cl.$^3$ .............................................. G01N 3/24
[52] U.S. Cl. ........................................ 73/845; 73/84; 73/841; 73/784
[58] Field of Search .................. 73/151, 84, 841, 845, 73/784

[56] References Cited

U.S. PATENT DOCUMENTS

| | | | |
|---|---|---|---|
| 2,927,459 | 3/1960 | Farrington | 73/784 |
| 2,957,341 | 10/1960 | Menard | 73/84 |
| 3,175,392 | 3/1965 | Tharalson | 73/84 |
| 3,562,916 | 2/1971 | Duckworth | 73/784 |
| 3,572,114 | 3/1971 | Ruppeneit et al. | |
| 3,796,091 | 3/1974 | Serata | |
| 4,075,885 | 2/1978 | Handy | 73/845 |

*Primary Examiner*—Howard A. Birmiel
*Attorney, Agent, or Firm*—Zarley, McKee, Thomte, Voorhees & Sease

[57] ABSTRACT

A device for determining the shear strength of rock and soil is disclosed. The device includes means for supporting the device within a borehole, a primary shaft, a plurality of shearing units slidably attached to the shaft having shear heads which are movable from a retracted position to a material-engaging expanded position, and a slip joint between adjacent shearing units such that the units operate independently from one another. The shearing units apply progressively greater normal forces on the material to be tested and sequentially shear the material being tested.

In operation, the device is lowered into a borehole. Then the shearing units are moved from their retracted position to their expanded material-engaging position so as to apply progressively greater normal forces on the material to be tested. An axial force is then applied to the shaft so that the material engaged by the shearing unit closest to the anchor shears. After the material shears, the respective heads of the shearing unit are retracted and the axial force is transferred to the next adjacent shearing unit by means of the slip joint. After the material engaged by each of the shearing units is successively sheared, the shearing characteristics of the material may be determined from the known applied normal and shear forces.

29 Claims, 15 Drawing Figures

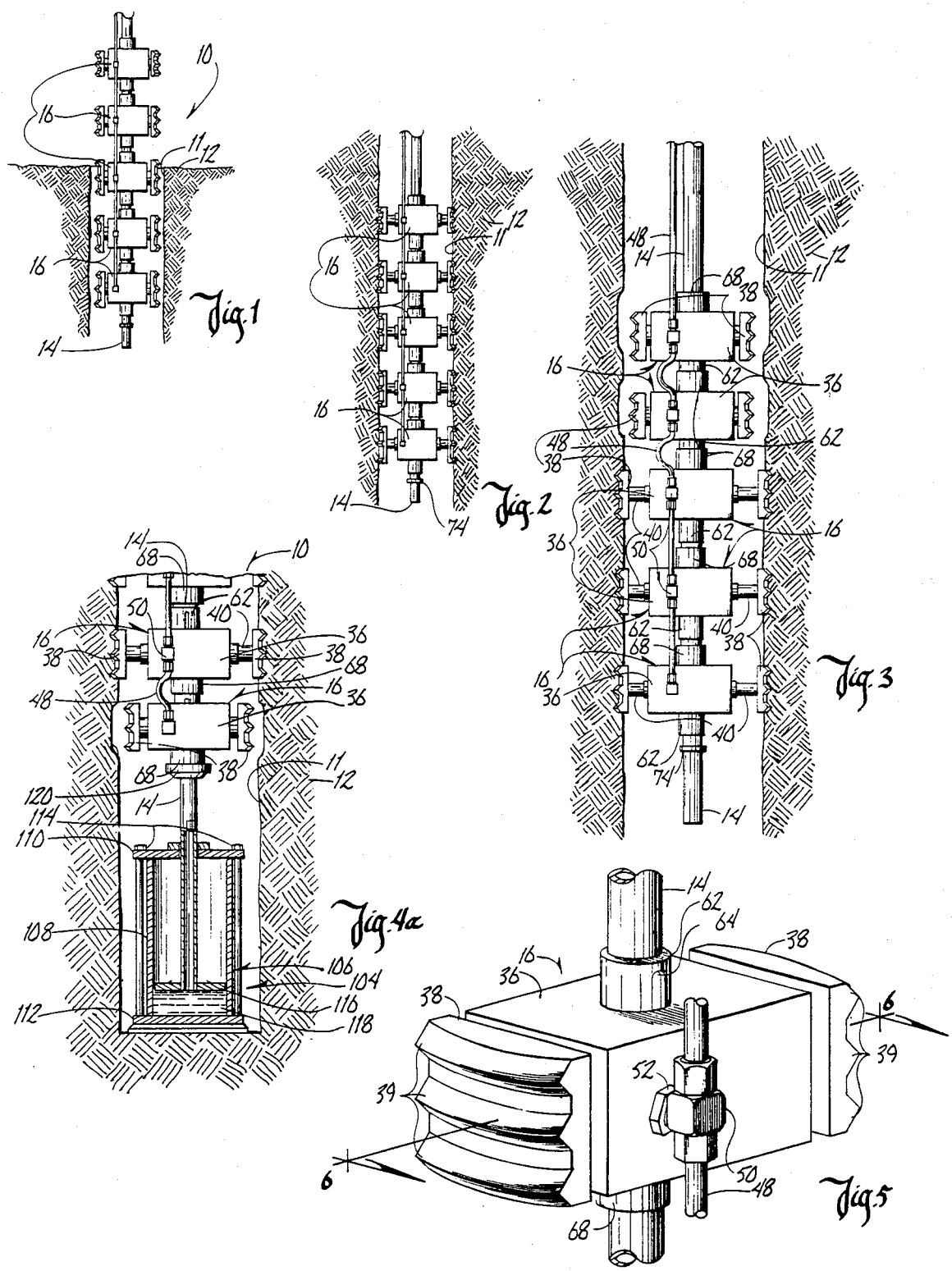

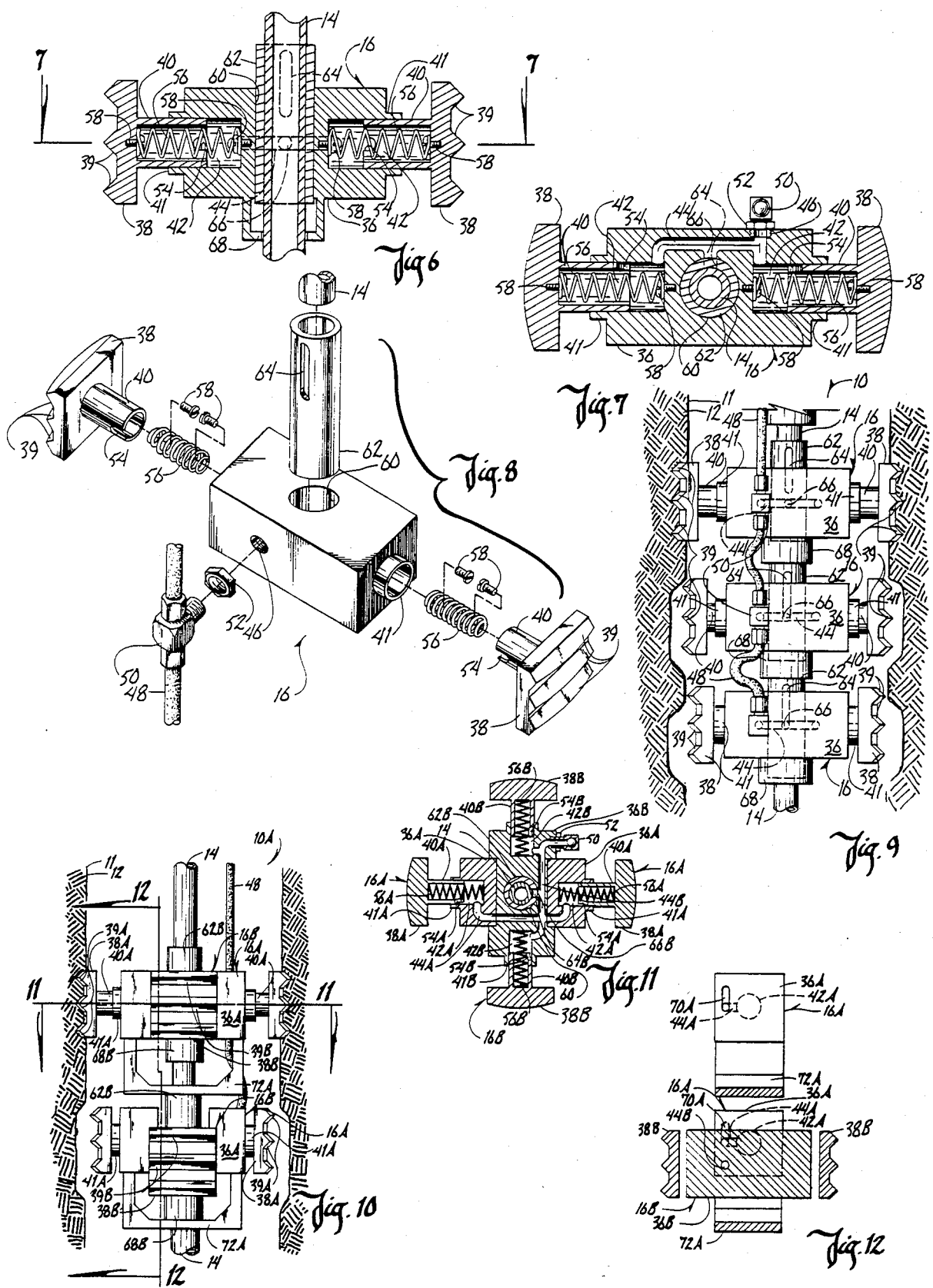

SOIL AND ROCK SHEAR TESTER

BACKGROUND OF THE INVENTION

Conventional devices for testing the shear strength of soil and/or rock in boreholes, such as that described in U.S. Pat. No. 4,427,871, are inadequate for use in heavily overconsolidated soils in which the vertical pressure is less than it was at some earlier time, such as glacial clays and tills. Generally, such devices are inserted into a borehole and a force normal to the longitudinal axis of the borehole is applied to the material being tested by a shear plate engaging such material, and then an axial force is exerted on the device until the material shears. The test zone is destroyed upon shear of the material, thus requiring the device to be repositioned into a fresh testing zone each time the axial force is applied. This procedure is time consuming and cumbersome, particularly when the material being tested is at a great depth from the land or water surface such as in off-shore drilling investigations.

Therefore a primary objective of the present invention is the provision of a soil and rock testing device having a plurality of independently acting shear heads for testing material surrounding a borehole without need for repositioning the device after the material shears adjacent one of said shear heads.

A further objective of the present invention is the provision of an in situ soil and rock testing device which can be used to test the material at various depths along a borehole.

A further objective of the present invention is the provision of a soil and rock testing device that can be used in determining the shear strength characteristics of the material being tested.

A further objective of the present invention is the provision of a soil and rock testing device which can be anchored anywhere along the length of a borehole.

A further objective of the present invention is the provision of a soil and rock testing device which is durable in use, and provides for easier and more rapid testing.

SUMMARY OF THE INVENTION

A device and method for determining the shear strength of rock and soil comprising anchoring means for supporting the device within a borehole, a shaft or woven wire cable attached to the shear head and having a longitudinal axis coextensive with that of the borehole, a plurality of shearing units attached to a central shaft and being movable within the borehole between a first retracted position and a second material-engaging expanded position, and a means for applying an axial force along the shaft sequentially to each of the shearing units so that the units successively shear the material to be tested. Each succeeding shearing unit acts independently of the other shearing units and each unit applies a force normal to the longitudinal axis of the borehole on the material to be tested progressively greater than that of the preceding shearing unit. The shearing units may be off-set at the same level on the shaft. After the material engaged by one shearing unit shears, the shear heads of that unit retract and the axial force on the shaft is transferred to the next adjacent shearing unit. The device thus permits testing of the material along the borehole at various levels therein without repositioning of the device in the borehole.

More particularly, the shearing units of the device each comprise a cylinder block mounted on the shaft and a pair of shear plates or heads mounted opposite one another on the cylinder block so as to define communicating fluid compartments for each head. Each of the shear heads has a plurality of horizontal teeth for engaging the material to be tested. Compressed gas or hydraulic fluid is introduced into the fluid compartments of the cylinder blocks so as to expand the shear heads from the first position to the second position. A retracting means includes a bleeder port to expel the compressed air from the air cylinders after the material to be tested shears and a tension spring to urge the shear heads towards one another after the air has been expelled from the air compartments. A slip joint is provided at each of the shearing units so that axial force can be sequentially transferred from one unit to the next adjacent unit after the material engaged by the former unit has sheared.

In operation, the shear testing device is introduced into the borehole, the shearing units are moved from the retracted position to the expanded position by introducing compressed air or hydraulic fluid into the fluid compartments and thereby applying normal forces on the material in the borehole to be tested, an axial force is applied along the shaft sequentially to each of the shearing units until the material engaged by each unit is sheared, the shear plates are retracted after the material engaged by the shearing unit has sheared, and then the shearing strength of the material to be tested is determined from the known applied normal and axial forces.

BRIEF DESCRIPTION OF THE DRAWINGS

FIG. 1 is an elevation view showing the device as it is introduced into the borehole with the shear heads in the retracted position.

FIG. 2 is an elevation view showing the device in position in a borehole with the shear heads in the expanded position before shearing of any material has occurred.

FIG. 3 is an elevation view showing the device in use with the upper shear heads in the retracted position after shearing of the adjacent material and the lower shear heads being in the expanded position prior to shearing of the adjacent material.

FIG. 4a is an elevation view of the device showing an axial shear force actuating means being positioned below the shearing units at the bottom of the borehole.

FIG. 4b is an elevation view of the device showing an alternative means for applying axial force using an anchoring shear head and actuating said piston for anchoring the device at any location along the borehole.

FIG. 5 is an enlarged perspective view of a first embodiment of a shearing unit employed when the device is anchored below the unit.

FIG. 6 is a sectional elevation view taken along line 6—6 of FIG. 5.

FIG. 7 is a sectional plan view taken along line 7—7 of FIG. 6.

FIG. 8 is an exploded perspective view of a shearing unit.

FIG. 9 is an elevation view similar to FIG. 4a showing the device at the various stages of transferring the axial force when anchored at the bottom of the borehole.

FIG. 10 is an elevation view of an alternative embodiment of the device at the various stages of material shear and having a pair of shearing units positioned at the same level on the shaft.

FIG. 11 is a sectional plan view of the device of the alternate embodiment taken along line 11—11 of FIG. 10.

FIG. 12 is a sectional elevation view taken along line 12—12 of FIG. 10.

DETAILED DESCRIPTION OF THE DRAWINGS

Figure 46:
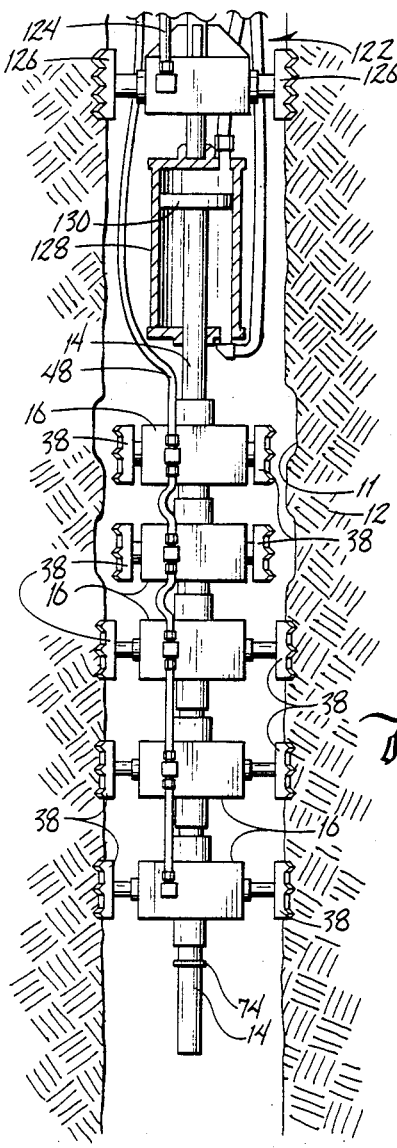

The rock and soil testing device of the present invention is generally designated by the numeral 10. The device is used to determine the shear strength of rock and overconsolidated soils by placing device 10 in a borehole 11, placing a normal stress perpendicular to the longitudinal axis of the borehole upon the adjacent soil or rock 12, and then applying an axial force to device 10 until the soil or rock material 12 shears. The shear strength characteristics of the material can then be determined from the known forces applied thereto using the well-known Mohr-Colomb failure theory.

More particularly, device 10 includes a hollow shaft 14, a plurality of shear units 16. As seen in FIGS. 5-8, the first embodiment of a shear unit 16 generally includes a cylinder block 36 and a pair of oppositely disposed shear heads 38 mounted upon cylinder block 36 having a plurality or horizontal linear teeth 39. The number of teeth, their height, angles, and spacing may vary depending upon the type of material to be tested. Each shear head has a curvature such that when the heads are in the retracted position, the radius of curvature at the apex of the teeth is equal to that of the borehole.

In the first shear unit embodiment 16 shown in FIGS. 6, 7 and 8, each shear head 38 is mounted on a shaft 40 which is journaled in collar 41 on cylinder block 36 so as to define an air or fluid compartment 42. The compartments formed by each shear head 38 on cylinder block 36 are interconnected by a passageway 44. A flexible hose 48 is threadably secured to hole 46 in cylinder block 36 by a standard fitting 50, which includes a conventional one-way check valve, and is in communication with compartments 42. A lock nut 52 secures fitting 50 to cylinder 36. Compressed air from a compressed air source (not shown) or hydraulic fluid is introduced into compartments 42 through flexible hose 48 so as to expand shear heads 38 outwardly from cylinder block 36. A slot 54 in each mounting shaft 40 permits air or fluid to enter compartments 42 when shear heads 38 are in a fully retracted position. A tension spring 56 secured at its opposite ends to cylinder block 36 and shear heads 38, respectively, with screws 58 serves to pull shear head 38 back into its retracted position when compressed air is released from compartment 42 as more fully described below.

Cylinder block 36 has a central hole 60 through which a bushing 62 is slidably mounted. Shaft 14 of device 10 is journaled within bushing 62, with the friction between bushing 62 and shaft 14 being less than that between bushing 62 and block 36. Bushing 62 includes a slot 64 which permits air to escape from compartment 42 when bleeder port 66 in passageway 44 aligns with the slot. A collar 68 is secured to cylinder block 36 so as to limit its movement with respect to bushing 62.

In operation, device 10 is lowered into borehole 11 with shear heads 38 in the retracted position. After the device is lowered to the desired depth, compressed air from a compressed air source (not shown) or hydraulic fluid is introduced via lines 48 into fluid compartments 42 in each of shear units 16. All shear heads 38 are simultaneously expanded into their soil-engaging position by the compressed air or hydraulic fluid to a known normal stress value.

The normal force applied to the material 12 to be tested is progressively increased from one shear unit 16 to another, with the smallest normal force being applied by the shear unit 16 nearest the upper end of device 10. While the compressed air or hydraulic source delivers the same gauge pressure to each shear unit 16, the normal force applied to the material 12 is progressively increased in each succeeding shear unit either by increasing the cross-sectional area of the individual compartments 42 in each successive shear unit 16 while maintaining the surface area of all shear heads 38 of device 10 equal to one another, or by maintaining the cross-sectional area of all the fluid compartments 42 of device 10 equal while increasing the surface area of the shear heads 38 on each successive shear unit 16. The normal force applied to the material being tested is the product of the gauge reading of the compressed air or hydraulic fluid source times the cross-sectional area of the cylinder block divided by the surface area of the shear head.

Each shear unit 16 acts independently from the other shear units with respect to he axial force applied to shaft 14. In other words, axial force is first applied to the shear unit nearest the axial force system until the material 12 engaged by teeth 39 of shear heads 38 of that unit shears. While the material adjacent the first shear unit closest to the axial force system shears, shear heads 38 of that shear unit 16 and the corresponding bushing 62 move in the direction of the axial force until bushing 62 contacts collar 68 of the next adjacent shear unit which prevents further movement of bushing 62. As shear continues, the shear unit continues to move until bleeder port 66 comes into communication with slot 64 in bushing 62 to release the compressed air from the compressed air compartments 42. As the air is released, springs 56 pull shear heads 38 into their retracted position and disengage teeth 39 from the material 12.

When the opposite end of bushing 62 comes into contact with collar 68 of the shear unit where material shearing has occurred, the axial force is transferred to the next adjacent unit. This sequence of successive retraction of shear heads and transfer of axial force is repeated at each successive shear unit after the material engaged thereby shears. It should be noted that only collar 68 of the first shearing unit closest to the axial force system is prevented from slipping with respect to shaft 14 so that axial force can be directly applied to that unit. Collar 68 of the remaining shear units slides with respect to shaft 14 and the axial force is applied to the remaining units through the first unit and all other units wherein material shear has occurred. A stop collar 74,, such as that shown in FIG. 3, causes bushing 62 of the last shear unit to move so that air can be expelled from air compartments 62 of that unit such that shear heads 38 of that unit can be retracted and device 10 can be removed from the borehole.

As seen best in FIG. 9, the material engaged by teeth 39 of the lowermost unit has sheared, as indicated by the recessed areas in borehole 11. Bushing 62 of the unit has contacted collar 68 of the middle shear unit shown so that bleeder port 66 has aligned with slot 64 to release the air compartments 42 so that shear heads 68 retract. Bushing 62 has also bottomed-out in collar 68 of the lowermost unit with collar 68 of the next adjacent unit coupled with the bottoming-out of bushing 62 in corresponding collar 68 of the same shear unit, transfers the axial force to the middle shear unit shown. As depicted, shearing has begun in the soil adjacent the middle unit and that unit continues its upward movement with respect to its bushing. Bleeder port 66 is partially aligned with slot 64 so that compressed air is expelled from air compartments 42 of middle unit 16. When bushing 62 of middle unit 16 finally bottoms-out in the collar of that unit, the axial force will be transferred to the next adjacent unit. This transfer of axial force from one shear unit to the next successive shear unit continues until the material engaged by the unit furtherest from the anchor shears, at which time the device can be removed from the borehole.

The slip joint provided by bushing 62 and collar 68 permits individual sequential testing of the material along borehole 11 without the need to reposition device 10 within the borehole. Because the normal force applied to the material is progressively greater with each successive shear unit, the axial force required to shear the adjacent material will be greater at each successive shear unit.

The orientation of bushing 62 and collar 68 with respect to borehole 11 is dependent upon the direction of the axial force. The axial force is preferably exerted on shaft 14 in such a direction that the shear unit closest to the axial force system, which also applies the smallest normal force on the material being tested, is the first to shear the material engaged thereby. The bushing and collar set of each shear unit is arranged such that the collar is on the side of the shear unit closest to the axial force system. This arrangement is seen in FIGS. 3 and 4. In FIG. 3, where shearing originates from the top of the borehole 11, collars 68 are on the top of each shear unit 16 while the corresponding bushings 62 extend below the shear unit. In comparison, FIG. 4a shows device 10 anchored at the bottom of borehole 11 and collars 68 are on the bottom side of each shear unit 16 while the corresponding bushings 62 extend above the shear unit.

An alternate embodiment 10A of the device is shown in FIGS. 10–12 in which a pair of shear units, 16A and 16B, are positioned on the device at the same level. The construction of shear unit 16A and 16B is generally the same as that described in the preferred embodiment. Shear unit 16A has a pair of cylinder blocks 36A while unit 16B has a cylinder block 36B. Each unit has a pair of oppositely disposed shear heads 38A and 38B with a plurality of teeth thereon 39A and 39B, respectively, and a similar spring retraction means 56A and 56B. The fluid compartments 42A and 42B intercommunicate via fluid passages 44A and 44B and are supplied with compressed air or hydraulic fluid via flexible hose 48 connected to one of the cylinder blocks by standard fitting 50 which has a one-way check valve. Shear head shafts 40A and 40B upon which the shear heads are mounted also include a slot 54A and 54B, respectively, so that air or fluid may enter compartments 42A and 42B when the heads are in their retracted position. Shafts 40A and 40B are slidably mounted within collars 41A and 41B of blocks 36A and 36B, respectively.

As in the preferred embodiment, each shear unit applies a progressively greater normal force upon the material to be tested than that of the previous adjacent shear unit. In the alternative embodiment, shear unit 16A closest to the anchor applies the smallest normal force while shear unit 16B at the same elevation applies a greater normal force to the material to be tested. The next successive pair of shearing units likewise each apply a greater normal force to the material to be tested than that of the preceding pair of shear units.

A modified slip joint arrangement permits the shear heads 38A to shear the engaged material and then be retracted before the axial force is transferred to the corresponding shear heads 38B at the same elevation. Fluid passage 44A of cylinder block 36A includes vertical extension 70A which permits release of the compressed air or hydraulic fluid therein after shear unit 16A has moved in response to the shearing of the material being tested. Before the unit moves, extension 70A is sealed off by cylinder 16B. After shear unit 16A moves above the level of shear unit 16B, extension 70A placed passage 44A in communication wth the atmosphere so as to expel the compressed air or fluid from compartment 42A such that heads 38A retract. When connecting member 72A (similar to collar 68 in the preferred embodiment contacts collar 68B attached to cylinder block 36B of shear unit 16B, the axial force is transferred to shear unit 16B. After shear unit 16B moves in response to the shearing of the adjacent material, bleeder port 66B of passage 44B comes into communication with slot 64B and bushing 62B so as to release the air or fluid from compartments 42B and retract shear heads 38B. Bushing 62B then bottoms-out in collar 68B so that the axial force can be transferred to the next adjacent set of shear units.

Figure 13:
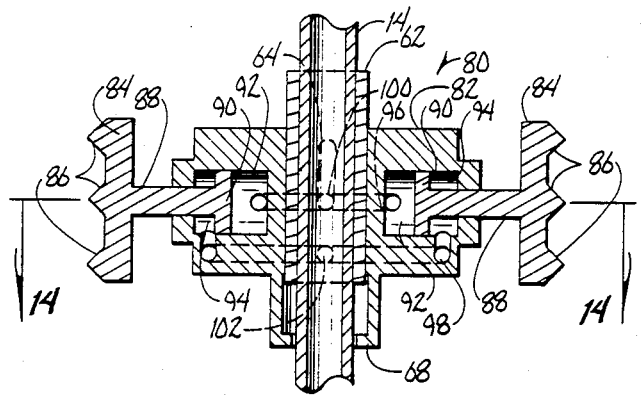
FIG. 13 is a sectional elevational view of a second embodiment for the shearing unit.
Figure 14:
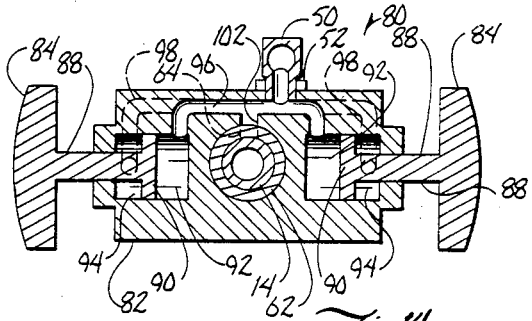
FIG. 14 is a sectional plan view of the second shearing unit embodiment.

A second shear unit embodiment 80 is shown in FIGS. 13 and 14. The second shear unit of embodiment 80 includes a cylinder block 82 and a pair of oppositely disposed shear head 84 mounted upon cylinder block 82 and having a plurality of horizontal linear teeth 86. Each shear head 84 is mounted on a piston rod 88 which extends into cylinder block 82 and terminates in a piston head 90 so as to define expansion fluid compartments 92 and retraction fluid compartments 94 within cylinder block 82. Expansion compartments 92 are interconnected by passageway 96 while retraction fluid compartments 94 are interconnected by passageway 98. Flexible hose 48 supplies compressed air for hydraulic fluid to expansion compartments 92 so as to extend shear heads 84 outwardly to apply radial pressure to borehole walls, as described previously with respect to first shear unit embodiment 16. The shear test then proceeds as previously described. As shear unit 80 continues to move after bushing 62 has contacted collar 68 of the next adjacent shear unit such that unit 80 moves with respect to bushing 62, slot 64 in bushing 62 aligns with bleeder port 100 in passageway 96 and bleeder port 102 in passageway 98 so as to provide communication therebetween. Such alignment of slot 64 thus provides communication between expansion compartments 92 and retraction compartments 94 such that the pressures within the two compartments are equalized. Because the pressure within expansion compartments 92 is much greater than that within retraction compartments 94 during the shear test of each particular shear unit 80, when slot 64 aligns with bleeder ports 100 and 102 so as to provide communication between the expansion and retraction compartments, the release of pressure from expansion compartments 92 to retraction compartments 94 causes shear heads 84 to be retracted such that the axial force can be transmitted to the next adjacent shear unit.

The axial force can be applied by any conventional means. For example, axial shear force may be applied to device 10 and individual shear units 16, 16A, 16B, or 80 by applying tension to central shaft 14 wherein the reaction occurs at the surface of the ground. Alternatively, an anchoring system positioned within borehole 11 may be used to provide reaction to produce axial shear force, as shown in FIGS. 4a and 4b. In FIG. 4a, a reaction foot 104 is used on the bottom of borehole 11 when a device cannot be anchored at the top or along the sides of the borehole, such as in off-shore drilling exploration. Reaction foot 104 includes a cylinder 106 having a side wall 108, a top 110, and a bottom 112 which rests against the floor of borehole 11. Cylinder 16 may be of integral construction or may be constructed with bolts 114 to provide sealing engagement of sidewall 108, top 110, and bottom 112. Shaft 14 of device 10 extends into the interior of cylinder 106. The lower end of shaft 14 of device 10 is connected to a pressure plate 116 within cylinder 106. A hydraulic fluid 118 is introduced into cylinder 106 via shaft 14 to force plate 116 and shaft 14 upwardly to apply the axial force necessary to shear material 12 being tested. A plate 120 is securely fixed to shaft 14 so that the axial force can be applied to the bottom of the adjacent shearing unit.

In FIG. 4b, a shear unit 122, similar in structure to first shear unit embodiment 16 or second unit embodiment 80, provides a normal force against the walls of the borehole which is much greater than that force exerted by any of the other shear units upon material 12 surrounding borehole 11. The relatively greater radial pressure of unit 122 is provided by providing a separate hydraulic line 124 with greater pressure to unit 122, by increasing the area of shear heads 126, or by increasing the cross-sectional area of the internal expansion chamber (not shown). Shear unit 122 can be positioned anywhere along the walls of borehole 11 with axial force being applied either upwardly or downwardly therefrom. The axial force is applied in a manner similar to that described with respect to reaction foot 104. More particularly, a hydraulic cylinder 128 having a piston 130 therein is adapted to receive hydraulic fluid from a hydraulic fluid source (not shown) so as to apply compressive axial force to shaft 14 in a direction away from shear unit 122 and in a quantity sufficient to shear material 12 being tested.

The number of shearing units and the spacing therebetween is dependent upon the desired tests and other practical considerations. It is also within the scope of this invention to rotate the position of the shear units with respect to one another along the longitudinal axis of shaft 14.

With the device of the present invention, the shear characteristics of the material to be tested can be determined from the known normal and axial forces applied to the material. Therefore, at least all of the stated objectives are accomplished.

What is claimed is:

1. A device for determining the shear strength of rock and soil, comprising:

anchoring means for supporting said device within a borehole drilled in the material being tested;
    a shaft slidably mounted to said anchoring means;
    a plurality of shearing units attached to said shaft, said units being movable within said borehole between a first retracted position and a second material-engaging expanded position, said shearing units applying progressively greater normal forces on the material being tested while in said expanded position; and
    means for sequentially applying an axial force along said shaft to each of said shearing units whereby said shearing units successively shear the material being tested.

2. The device according to claim 1 wherein said shear heads of all of said shearing units expand from said retracted position to said expanded position simultaneously.

3. The device according to clam 1 wherein said anchoring means is a shearing unit applying a normal force on the material being tested greater than that applied by any other shearing unit.

4. The device according to claim 1 wherein more than one of said shearing units are mounted at the same level on said shaft.

5. The device according to claim 1 wherein said shearing units are sequentially mounted on said shaft with only one of said units at any particular level on said shaft.

6. The device according to claim 1 wherein said means for sequentially applying an axial force along said shaft to each of said shearing units is a slip joint between adjacent shearing units operative such that said units slip successively to transfer the axial force to the next succeeding shearing unit as the material engaged by the preceding shearing unit shears.

7. The device according to claim 1 wherein each of said shearing units comprises a cylinder block slidably mounted on said shaft and a pair of shear heads mounted opposite one another on said block so as to define an expansion compartment within said cylinder block, each of said shear heads having a plurality of horizontal teeth for engagement with the material being tested.

8. The device according to claim 7 further comprising a means for supplying fluid under pressure to said compartment whereby said shear heads expand from said retracted position to said expanded position.

9. The device according to claim 8 wherein said means for supplying fluid under pressure to said expansion compartment includes a flexible hose in communication with each of said compartments and in communication with a source of such fluid.

10. The device according to claim 7 further comprising a retracting means for retracting said shear heads from said expanded position to said retracted position.

11. The device according to claim 10 wherein said retracting means includes a bleeder port to expel the compressed fluid from said expansion compartment after the material being tested shears and a tension spring to urge said shear heads into said retracted position when the fluid is expelled fom said expansion compartment.

12. The device according to claim 10 wherein said retracting means includes a retraction compartment within said cylinder block and a passageway within said cylinder block providing communication between said expansion and retraction compartments after the material being tested shears such that the compressed fluid is expelled from said expansion compartment into said retraction compartment thereby urging said shear heads into said retracted position.

13. The device according to claim 7 wherein said compartments of successive shearing units have progressively larger cross-sectional areas and said shear heads of successive shearing units have equal surface areas such that as compressed fluid is supplied to said air compartments, the normal force exerted on the material being tested becomes progressively greater with each successive shearing unit.

14. The device according to claim 7 wherein said compartments of successive shearing units have equal cross-sectional areas and said shear heads of successive shearing units have progressively larger surface areas such that as compressed fluid is supplied to said compartments, the normal force exerted on the material being tested becomes progressively greater with each successive shearing unit.

15. A device for determining the shear strength of rock and soil, comprising:
  anchoring means for supporting said device within a bore drilled in the material being tested, said borehole having a longitudinal axis;
  a shaft slidably mounted on said anchoring means and having a longitudinal axis coextensive with said longitudinal axis of said borehole;
  a plurality of cylinder blocks slidably mounted on said shaft;
  a pair of shear heads mounted opposite one another on each of said cylinder blocks so as to define an expansion compartment within said cylinder block, each of said shear heads having a plurality of teeth for engagement with the material to be tested;
  a fluid supply means for providing compressed fluid to said expansion compartments whereby each of said pairs of shear heads is expanded simultaneously from a first retracted position to a second expanded positon;
  said shear heads of each successive shearing unit applying progressively greater normal force on said material being tested while in said expanded position;
  means for applying an axial force along said shaft to each of said shearing units;
  a shear head retracting means for retracting said shear heads from said expanded position to said retracting position after the material engaged by said teeth of said shear head shears; and
  means for sequentially transferring said axial force from one pair of shear heads to the next succeeding pair of shear heads after the material engaged by the preceeding pair of shear heads shears.

16. The device according to claim 15 wherein only one of said pair of shear heads is at any particular level with respect to said shaft.

17. The device according to claim 15 where more than one of said pair of shear heads at the same level with respect to said shaft.

18. The device according to claim 15 wherein said means for sequentially transferring an axial force along said shaft to each of said shear heads is a slip joint between adjacent cylinder blocks operative such that said units slip successively to transfer the axial force to the next succeeding pair of shear heads after the material engaged by the preceding pair of shear heads shears.

19. The device according to claim 15 wherein said cylinder blocks of successive shearing units have progressively larger cross-sectional areas and said shearing heads of successive shearing units have equal surface areas so that as compressed fluid is supplied to said compartments, the normal force exerted on the material being tested becomes progressively greater with each successive shearing unit.

20. The device according to claim 15 wherein said cylinder blocks of successively shearing units have equal cross-sectional areas and said shearing heads of successive shearing units have progressively larger surface areas so that as compressed fluid is supplied to said compartments, the normal force exerted on the material being tested becomes progressively greater with each successive shearing unit.

21. A method of in situ determination of soil and rock properties by drilling a borehole in the material to be tested, comprising:
  introducing into said borehole a device for determining the shear strength of the material to be tested, said device including an anchoring means for supporting said device within said borehole, a shaft slidably attached to said anchoring means having a longitudinal axis coextensive with that of said borehole, a plurality of shearing units slidably attached to said shaft, and means for sequentially applying an axial force along said shaft to each of said shearing units, each of said shearing units having a cylinder block slidably mounted on said shaft and a pair of shear heads slidably mounted opposite one another on said cylinder block so as to define an expansion compartment within said cylinder block, said shear heads being movable between a first retracted position and a second material-engaging expanded position;
  anchoring said device with respect to said borehole;
  moving said shearing heads of all of said shearing units from said retracted position to said expanded position simultaneously;
  applying normal forces on the material to be tested, said normal force being progressively greater at each succeeding shearing unit;
  sequentially applying an axial force along said shaft to each of said shearing units until the material engaged by said pair of shear heads of each unit is successively sheared;
  moving each pair of shear heads from said expanded position to said retracted position after the material engaged by said pair of shear heads has sheared; and
  determining the shearing strength of the material to be tested from the known applied normal and shear forces.

22. The method of claim 21 wherein said shear heads are moved from the retracted position to the expanded position by introducing compressed fluid into said compartments of each of said shearing units to expand said shear heads into engagement with the material to be tested.

23. The method of claim 21 wherein said shear heads are moved from the expanded position to the retracted position by expelling the compressed fluid from said expansion compartment and urging said pair of shear heads into said retracted position by spring means.

24. The method of claim 21 wherein said shear heads are moved from the expanded position to the retracted position by expelling the compressed fluid from said expansion compartment to a retraction compartment thereby urging said shear heads into said retracted position.

25. The method of claim 21 wherein the normal forces are applied by introducing compressed fluid into said compartments of each of said shearing units.

26. The method of claim 25 wherein the cross-sectional area of said compartments in each successive shearing unit is greater than that in the previous shearing unit whereby the normal force applied to the material being tested is progressively greater at each successive shearing unit.

27. The method of claim 25 wherein the surface area of each pair of shear heads is larger in each successive shearing unit than in the previous unit whereby the normal force applied to the material being tested is progressively greater at each successive shearing unit.

28. The method of claim 21 wherein said axial force is applied by a hydraulic system.

29. The method of claim 21 wherein the axial force is sequentially applied to successive shearing units by a slip joint between adjacent shearing units operative such that said shearing units successively slip to transfer the axial force from one shearing unit to the next successive unit as the material engaged by the preceding unit shears.

* * * * *